US00PP14500P29

(12) United States Plant Patent
Orard

(10) Patent No.: US PP14,500 P2
(45) Date of Patent: Feb. 3, 2004

(54) SHRUB ROSE PLANT NAME 'ORAPAYMEL'

(50) Latin Name: *Rosa hybrida*
Varietal Denomination: ORApaymel

(75) Inventor: Pierre Orard, Feyzin (FR)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 2 days.

(21) Appl. No.: 10/243,163

(22) Filed: Sep. 13, 2002

(51) Int. Cl.[7] ..... A01H 5/00
(52) U.S. Cl. ..... Plt./108

(58) Field of Search ..... Plt./108

(56) References Cited

PUBLICATIONS http://www.helpmefind.com/rose/pl.php?n=39715.*

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

A new variety of Shrub rose suitable for garden decoration, having flowers of white edged red coloration.

1 Drawing Sheet

Botanical designation: *Rosa hybrida.*

BACKGROUND OF THE INVENTION

This invention relates to a new and distinct variety of Shrub Rose. The varietal denomination of the new variety is 'ORApaymel'. It has as its seed parent the variety known as 'MEIdanu' (not patented) and as its pollen parent the variety known as 'KORbin' (not patented).

SUMMARY OF THE INVENTION

Among the features which distinguish the new variety from other presently available and commercial rose cultivars known to the inventor are the following combination of characteristics: its sepals whose inside surface darkens as the flowers age, its numerous stipitate glands, which have a moderate moschata fragrance, on the peduncle and on the surface of the bud, its red coloration that blushes darker as the flowers age and its many stipitate glands on the upper and under side of the rachis. The plant has a bushy to somewhat spreading and rounded growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'ORApaymel' may be asexually propagated by cuttings, budding and grafting.

COMPARISON WITH PARENTS

The new rose may be distinguished from its seed parent, 'MEIdanu' by the following combination of characteristics: whereas 'ORApaymel' bears semi-double (about 18 to 22 petals) flowers of white edged red coloration, 'MEIdanu' bears double flowers with significantly higher petalage (about 35 petals) of even dark red coloration. The new variety has a bushy to somewhat spreading and rounded medium height mature growing habit, whereas the seed parent has a more compact significantly shorter mature growth habit.

The new variety may be distinguished from its pollen parent, 'KORbin' by the following combination of characteristics: whereas 'ORApaymel' bears flowers of white edged red coloration, 'KORbin' bears flowers of white coloration. The pollen parent bears somewhat small light green foliage and new shoots, whereas 'ORApaymel' bears significantly larger significantly darker green foliage with very dark red new shoots.

BRIEF DESCRIPTION OF THE ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of August. Phenotypic expression may vary with environmental, cultural and climatic conditions, as well as differences in conditions of light and soil.

FLOWER

The new variety sometimes bears its flowers singly, usually in clusters of two to five or more per stem. Flowers may be borne in somewhat regular rounded clusters on medium length stems (about 32 to about 76 cm.). Outdoors, the plant blooms abundantly and nearly continuously during the growing season. The flowers have a slight tea fragrance.

BUD

The peduncle is about 2.2 to about 4.6 cm. in length, of average caliper (about 0.2 to about 0.3 cm. in diameter), and usually erect. It is moderately rough, with numerous stipitate glands. The stipitate glands bear a moderate moschata fragrance. Peduncle color is between 144B and 146B sometimes lightly suffused, especially on the side exposed to the sun, with between 183C and 187C.

Before the calyx breaks, the bud is about 1.2 to about 1.6 cm. in diameter at the widest point, about 1.6 to about 2.0 cm. in length, and very pointed to somewhat ovoid in shape. The surface of the bud bears very few foliaceous appendages and numerous stipitate glands, usually with slender entire foliaceous parts extending beyond the tip of the bud about ¼ or more of its length. The stipitate glands bear a moderate moschata fragrance. Bud color is between 144A and 146B sometimes lightly suffused, especially on the side exposed to the sun, with between 183C and 187C.

The sepals are about 2.6 to about 3.0 cm. in length and about 0.7 to about 0.9 cm. in width at the widest point. The outer surface of the sepal is between 144A and 146B sometimes lightly suffused, especially on the side exposed to the sun, with between 183C and 187C. The inner surface of the sepal is between 138A and 137C sometimes lightly suffused with between 183C and 187C that blush to between 187B and 187A as the flower ages. They are covered with fine wooly tomentum; sepal margins are lined with many stipitate glands and hairs.

As the petals open (after the calyx breaks), the bud is about 1.6 to about 2.3 cm. in diameter at the widest point, about 1.8 to about 2.7 cm. in length, and pointed to somewhat ovoid in form. The color on the upper surface of the newly opened petals, at the point where the petal attaches, is between 12A and 9C that gradually blushes to between 43D and 41D at the center of the petal to as dark as between 53A and 46A toward the very edge of the petal. The color on the under surface of the newly opened petals, at the point where the petals attaches, is between 12B and 10B that gradually suffuses to the edge of the petal with between 20C and 10D and sometimes blushes on areas exposed to the sun with as dark as between 53C and 46A.

BLOOM

When fully open, the bloom ranges from about 6.8 to about 8.3 cm. in diameter. Petalage is semi-double with about 18 to 22 petals and about 1 to 6 petaloids irregularly arranged. When partially open, the bloom form is somewhat high centered to cupped, and the petals moderately loosely spiraled to slightly cupped with petal edges somewhat reflexed outward. When fully open, the bloom form is more cupped, and the petals are more loosely cupped with petal edges somewhat reflexed outward.

PETALS

The substance of the petals is moderately heavy to somewhat leathery and of medium thickness, with upper surfaces slightly shiny to somewhat satiny and under surfaces slightly shiny to matte. The outer petals are nearly round to somewhat oval in shape with rounded apices. The inner petals are moderately obovate to somewhat oval in shape with rounded apices. The petals are about 3.0 to about 4.0 cm. in length and about 2.9 to about 4.0 cm. in width at the widest point. Petal margins are entire.

NEWLY OPENED FLOWER

The under surface of the outer, intermediate and inner petals is between 155A and 155B sometimes blushed on areas exposed to the sun with as dark as between 53A and 60A. At the point where the petal attaches, there is a small zone of between 9B and 7A.

The upper surface of the outer, intermediate and inner petals is between 155A and 155B that gradually blushes near the center of the petal with between 57A and 60D to as dark as between 53A and 45A toward the very edge of the petal. At the point where the petal attaches, there is a moderately large zone of between 12B and 12C.

The general tonality of the newly opened flower is between 155A and 155B that gradually blushes near the center of the petal with between 57A and 60D to as dark as between 53A and 45A toward the very edge of the petal.

THREE-DAY-OLD FLOWER

The under surface of the outer and inner petals is near 155C sometimes blushes on areas exposed to the sun with as dark as between 53A and 60A. There is no visible change in coloration at the point where the petal attaches.

The upper surface of the outer and inner petals is between 155C and 155D that gradually blushes toward the very edge of the petal with between 53A and 45A. At the point where the petal attaches, there is a very small zone of near 10D.

The general tonality of the three-day-old flower is between 155C and 155D that gradually blushes toward the very edge of the petal with between 53A and 45A.

On the spent bloom, the petals usually drop off cleanly. In August in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens vary in number (average about 83) and are arranged regularly about the pistils; a few are mixed with petaloids. The filaments are of medium-short length (about 0.4 to about 0.7 cm.), most with anthers. Filaments are between 12B and 9B in color. The anthers are moderately small for the class and all open approximately at the same time. Anther color is between 22A and 24B when immature and between 165B and 165A at maturity. Pollen is abundant.

FEMALE REPRODUCTIVE ORGANS

Pistils vary in number (average about 80). The styles are moderately uneven, average in length (about 0.4 to about 0.7 cm.), average in caliper, and somewhat loosely bunched. Stigma color is 7B and 8A. Style color is between 1C and 1D sometimes lightly suffused with near 53D. Ovaries are usually all enclosed in the calyx.

Hips are of moderately short length (about 1.3 to about 1.7 cm.), somewhat flat to globular in form, and between 28B and 30B in color when ripe. The hip surface is smooth with thick fleshy walls. The sepals are somewhat permanent and usually straight in shape. The seeds are irregularly rounded, smooth in texture, approximately 5 to about 12 per hip, about 0.3 to about 0.5 cm. in diameter at the widest point and between 160C and 162C in color.

FOLIAGE

The compound leaves are usually comprised of three to seven leaflets and are borne abundantly. The seven-leaflet leaves are about 8.2 to about 13.1 cm. in length and about 6.4 to about 9.9 cm. in width at the widest point, moderately leathery in texture, and semi-glossy in finish. The terminal leaflets are about 3.6 to about 5.9 cm. in length and about 2.2 to about 3.5 cm. in width at the widest point, shaped ovate to somewhat oval with somewhat acuminate to moderately acute apices and rounded bases. Their margins are usually simply serrate.

The upper surface of the mature leaf is between 146A and 147A. The under surface of the mature leaf is 146B and 147B. The upper surface of the young leaf is between 144A and 146B, usually heavily suffused with between 187A and 183A. The under surface of the young leaf is between 144B and 146B, usually heavily suffused with between 187B and 183B.

The rachis is light in caliper and rough. The upper side is shallowly grooved with many stipitate glands on the edges of the grooves. The under side of the rachis is rough with many stipitate glands and some small prickles. The rachis color is between 145B and 144C.

The stipules are about 1.1 to about 1.6 cm. in length and moderately narrow width (about 0.3 to about 0.5 cm.) with moderately long straight points that usually turn out at an angle of more than 45 degrees. The stipules color is between 146B and 146C.

The petiole is about 1.0 to about 1.8 cm. in length and about 0.1 to about 0.2 cm in diameter at the widest point. The petiole color is between 145B and 144C.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy to somewhat spreading and rounded medium height growing habit (about 108 to about 125 cm. in height and about 108 to about 125 cm. spread at the widest point), with very full branching. It displays moderately vigorous growth and the canes are of somewhat light to medium caliper for the class.

The color of the major stems is between 146D and 144C. They bear some medium size prickles that are about 0.2 to about 0.4 cm. in length. The prickles are hooked slightly downward with a medium length somewhat narrow oval base; prickle color is between 164A and 166B. The major stem bears no small prickles.

The color of the branches is between 144A and 147A. They bear some medium size prickles which are about 0.4 to about 0.7 cm. in length and of similar shape to the prickles on the major stems; prickle color is between 182B and 185C at the base and near 162B near the tip. The branches bear few small prickles of similar shape and coloration.

The color of the new shoots is between 144A and 146A usually heavily suffused with between 183A and 187A. They bear some medium size prickles which are of similar size and shape to the prickles on the branches; prickle color is between 187A and 183A. The shoots bear some small prickles of similar shape and coloration.

I claim:

1. A new and distinct Shrub rose plant of the variety substantially as described and illustrated herein.

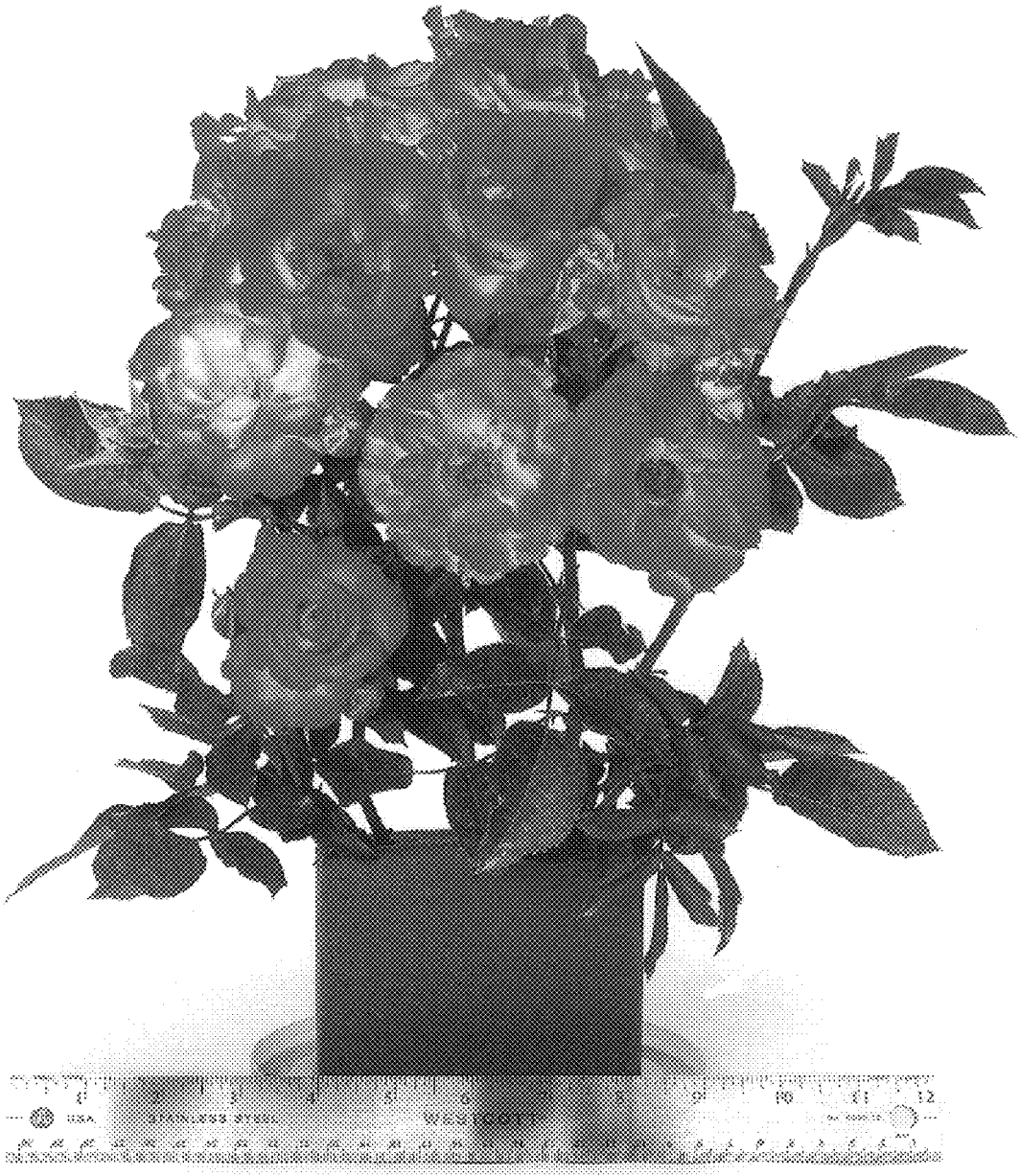

* * * * *